US008394320B2

(12) United States Patent
Sasaguri et al.

(10) Patent No.: US 8,394,320 B2
(45) Date of Patent: **\*Mar. 12, 2013**

(54) METHOD OF PRESERVING BIOMATERIAL

(75) Inventors: Shiro Sasaguri, Nankoku (JP); Hironori Maeda, Nankoku (JP); Munetoshi Kawamura, Kochi (JP)

(73) Assignees: Kochi University, Kochi (JP); Yugengaisha Sun World Kawamura, Kochi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/666,987

(22) PCT Filed: Jun. 25, 2008

(86) PCT No.: PCT/JP2008/001660
§ 371 (c)(1),
(2), (4) Date: Dec. 28, 2009

(87) PCT Pub. No.: WO2009/001561
PCT Pub. Date: Dec. 31, 2008

(65) Prior Publication Data
US 2010/0209291 A1    Aug. 19, 2010

(30) Foreign Application Priority Data
Jun. 28, 2007   (JP) ................... 2007-170262

(51) Int. Cl.
*A61L 2/00* (2006.01)
*A21D 4/00* (2006.01)
(52) U.S. Cl. ......................................... 422/22; 426/327

(58) Field of Classification Search ................... 422/22; 426/327
See application file for complete search history.

(56) References Cited

U.S. PATENT DOCUMENTS

| 6,451,364 B1 | 9/2002 | Ito | |
|---|---|---|---|
| 2003/0068414 A1* | 4/2003 | Ito | ................................ 426/237 |
| 2006/0233925 A1 | 10/2006 | Kawamura | |

FOREIGN PATENT DOCUMENTS

| JP | 62-297677 A | 12/1987 |
|---|---|---|
| JP | S62-297677 A | 12/1987 |
| JP | H5-306414 A | 11/1993 |
| JP | H6-257924 A | 9/1994 |
| JP | H7-155154 A | 6/1995 |

(Continued)

OTHER PUBLICATIONS

Notification of transmittal of Translation of the International Preliminary Report on Patentability (Forms PCT/IB/338) of International Application No. PCT/JP2008/001660 mailed Feb. 4, 2010 with Forms PCT/IB/373 and PCT/ISA/237.

(Continued)

*Primary Examiner* — Kevin C Joyner
(74) *Attorney, Agent, or Firm* — DLA Piper LLP (US)

(57) ABSTRACT

A method of preserving a biomaterial according to the present invention includes the step of simultaneously applying negative DC voltage and AC voltage to a biomaterial (O). It is preferable that in the simultaneous voltage application step, the biomaterial (O) is stored in a container (1) that surrounds at least the periphery of the biomaterial (O), and a voltage application plate (2) supplied with negative DC voltage and AC voltage in a superposed manner is placed along one outer surface of the container (1), so that the voltage is indirectly applied to the biomaterial (O).

5 Claims, 8 Drawing Sheets

FOREIGN PATENT DOCUMENTS

| | | |
|---|---|---|
| JP | H7-69105 B | 7/1995 |
| JP | 11-056319 A | 3/1999 |
| JP | 2002-34531 A | 2/2000 |
| JP | 2000-157159 A | 6/2000 |
| JP | 2001-149773 A | 6/2001 |
| JP | 2001-241824 A | 9/2001 |
| JP | 2002-100493 A | 4/2002 |
| JP | 2005-112839 A | 4/2005 |
| JP | 2006-217832 A | 8/2006 |
| JP | 2007-182390 A | 7/2007 |
| JP | 2007-295802 A | 11/2007 |
| WO | 98/41115 A1 | 9/1998 |
| WO | WO 98/41115 A | 9/1998 |
| WO | 2005/013730 A1 | 2/2005 |
| WO | WO 2006/011264 A | 2/2006 |
| WO | WO 2006/085534 A | 8/2006 |
| WO | WO 2006/100740 A | 9/2006 |

OTHER PUBLICATIONS

International Search Report of PCT/JP2008/001660, mailing date of Aug. 12, 2008.

* cited by examiner

METHOD OF PRESERVING BIOMATERIAL

TECHNICAL FIELD

The present invention relates to a method of preserving a biomaterial including blood, cells, tissues, and organs.

BACKGROUND ART

A conventional method of preserving a microorganism and animal derived material is disclosed, according to which AC or negative DC voltage in the range from 100 V to 5000 V is applied across an electrode to generate an electrostatic field atmosphere, and a microorganism or animal derived material is placed in the electrostatic field atmosphere at −20° C. to −40° C. for preservation. In this way, the microorganism or animal derived material is preserved in the electrostatic field atmosphere with the AC or negative DC voltage in the range from 100 V to 5000 V, preferably from 100 V to 3000 V, so that the microorganism or animal derived material can be preserved without inactivating or deactivating its activity or killing it (see for example JP 2005-112839 A).

DISCLOSURE OF THE INVENTION

According to the conventional preservation method, however, as for application of current/voltage, the current may be either AC or DC, and an effective voltage application method is not particularly specified other than voltage values such as 100 V, 500 V, and 1000 V. Furthermore, the conventional preservation method described above is mainly directed to how to preserve a microorganism or animal derived material in a state near its natural state for a long period without inactivating or deactivating the activity of the material or killing it. Therefore, the method does not sufficiently address the problem of inhibiting oxidization and cell damage caused by preservation.

In order to solve the above-described problem, the following measures (1) to (3) are employed according to the present invention. More specifically, (1) A method of preserving a biomaterial O according to the present invention includes the step of simultaneously applying negative DC voltage and AC voltage to the biomaterial O.

In particular, the absolute values of the DC voltage and AC voltage preferably do not exceed 5000 V.

(2) In the method of preserving a biomaterial O, in the simultaneous voltage application step, it is preferable that the biomaterial O is stored in a container 1 that surrounds at least the periphery of the biomaterial O and a voltage application plate 2 supplied with negative DC voltage and AC voltage in a superposed manner is (directly or indirectly) laid along one outer surface of the container 1, so that the biomaterial O is indirectly provided with the voltage.

(3) In any of the methods of preserving a biomaterial O, in the simultaneous voltage application step, it is preferable that the container 1 made of a conductive maternal and having a thickness of at least 10 mm (at least 10 mm for the bottom thickness, and at least 15 mm for the wall thickness, preferably about 15 mm for both the bottom thickness and the wall thickness) that stores the biomaterial O therein is laid on the voltage application plate 2 supplied with the negative DC voltage and the AC voltage in a superposed manner.

In this way, dissolved oxygen in the biomaterial O being preserved is inactivated, so that oxidizing and reduction of cell damage that could be caused by the preservation can be inhibited or reduced more effectively.

BEST MODE FOR CARRYING OUT THE INVENTION

Embodiments of the present invention will be described in detail in conjunction with the accompanying drawings, in which the same or corresponding portions are designated by the same reference characters, and their description will not be repeated.

Figure 1:
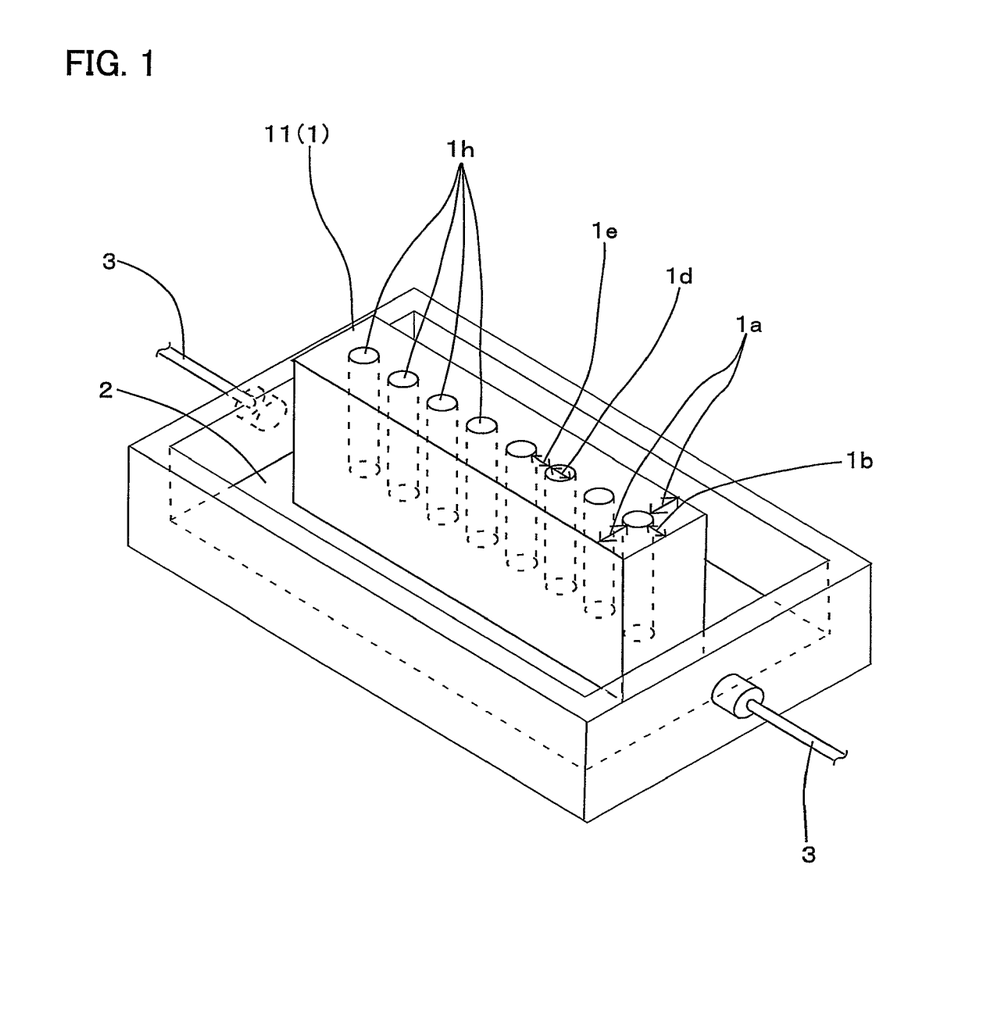
FIG. 1 is a perspective view showing an example of the state of an application plate, a container, and an electrode during preservation process in a method of preserving a biomaterial according to Example 1.
Figure 2:
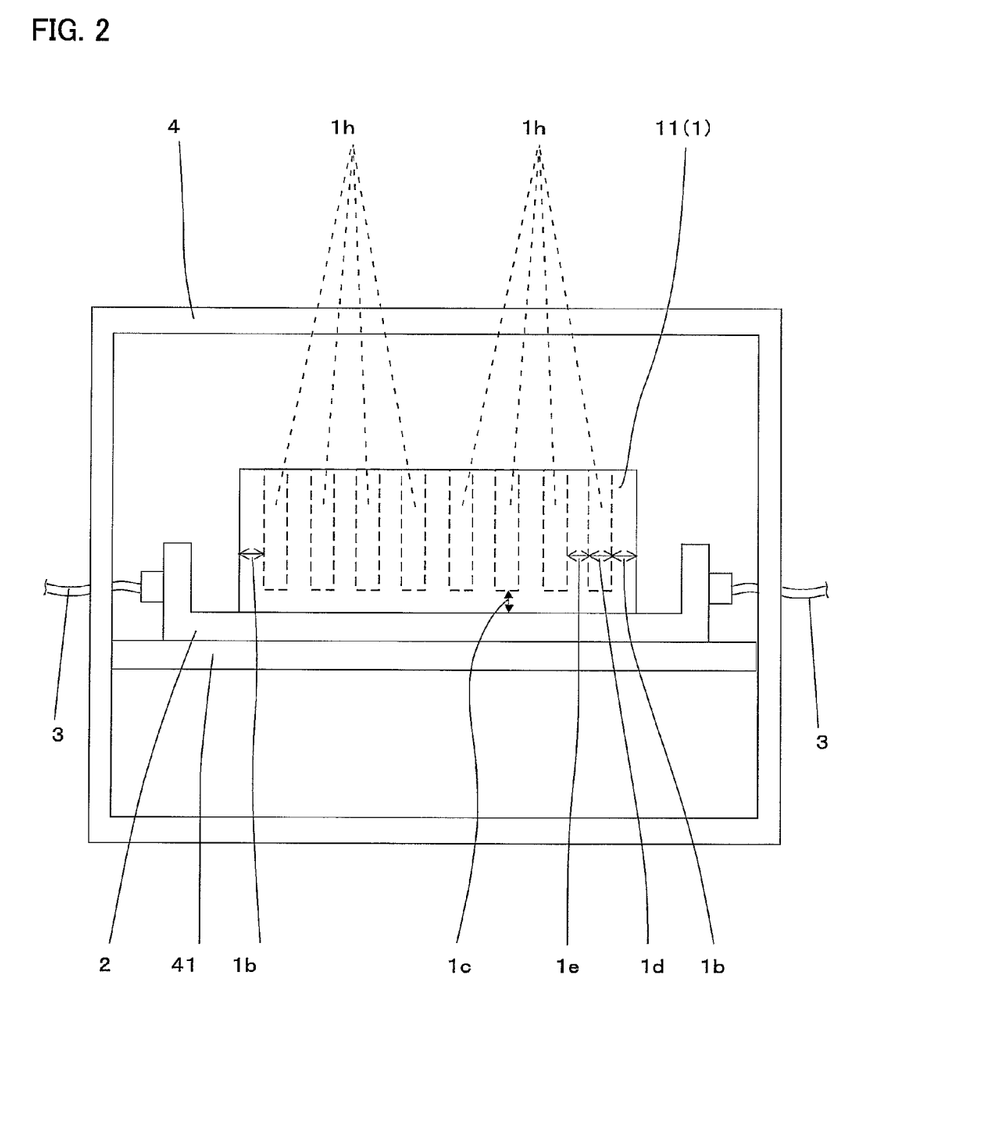
FIG. 2 is a front sectional view showing the entire structure including a storage in addition to the example according to Example 1 in FIG. 1 during preservation process.
Figure 3:
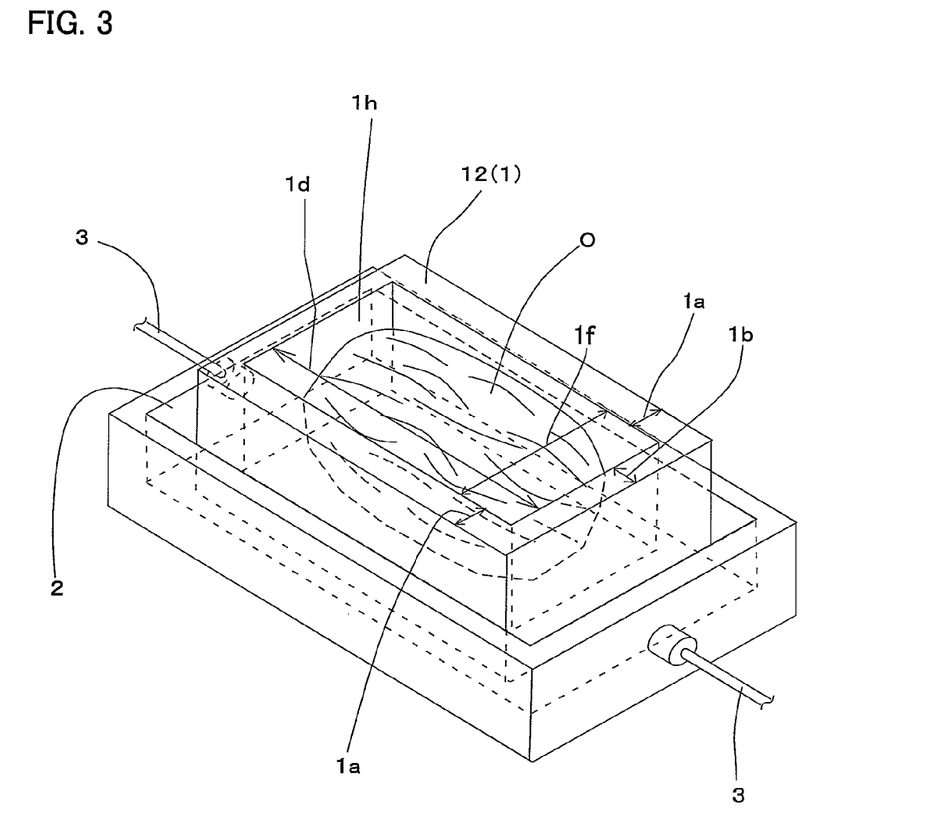
FIG. 3 is a perspective view showing an example of the state of an application plate, a container, and an electrode during preservation process in a method of preserving a biomaterial according to Example 2.
Figure 4:
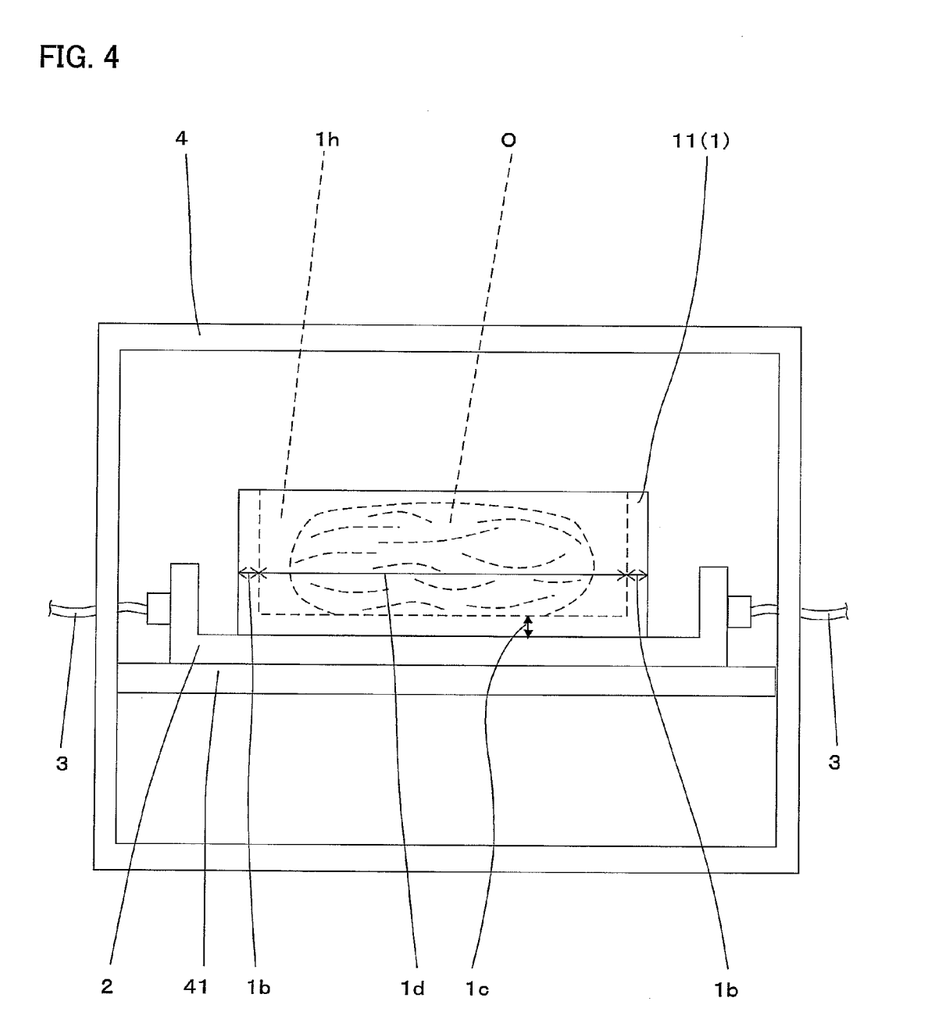
FIG. 4 is a front sectional view showing the entire structure including a storage in addition to the example according to Example 2 in FIG. 3 during preservation process.
Figure 5:
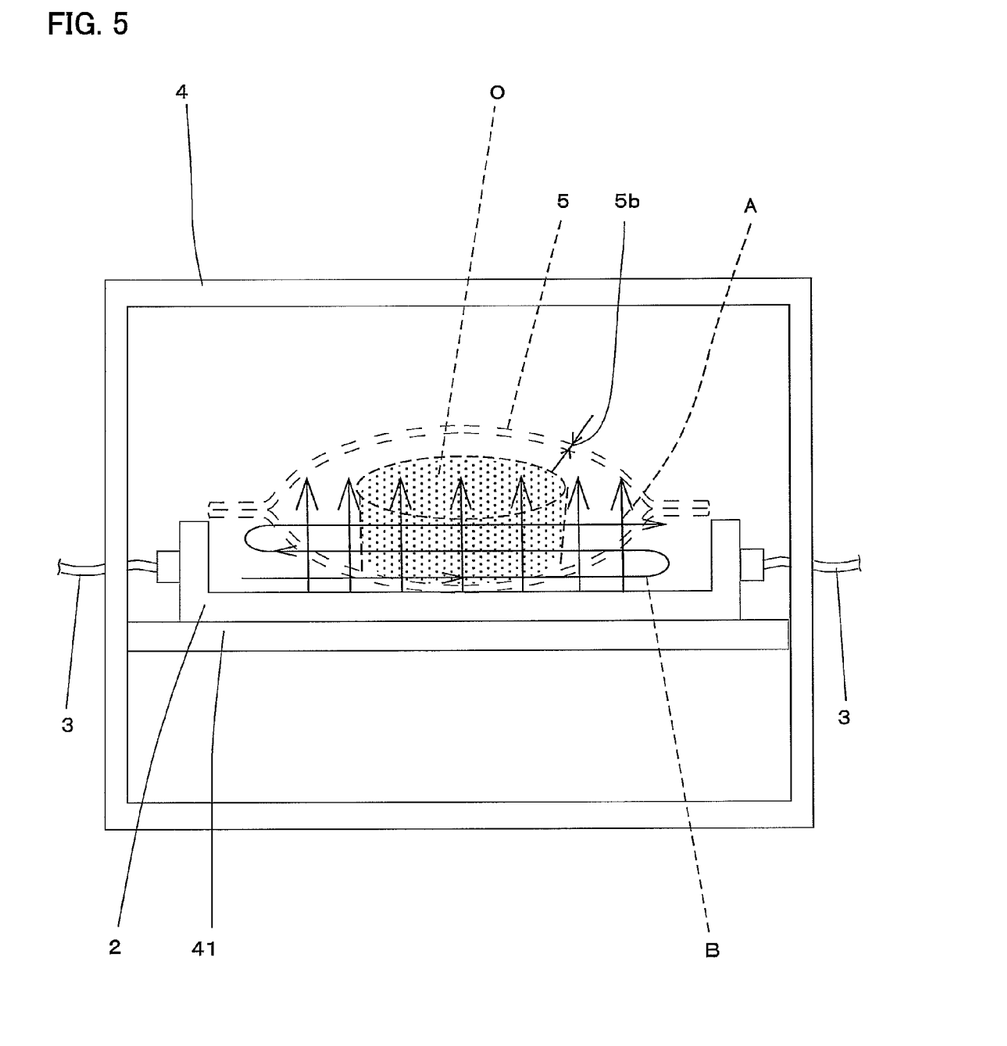
FIG. 5 is a concept view showing the entire structure (including a storage) during preservation process in a method of preserving a biomaterial according to Example 3.
Figure 6:
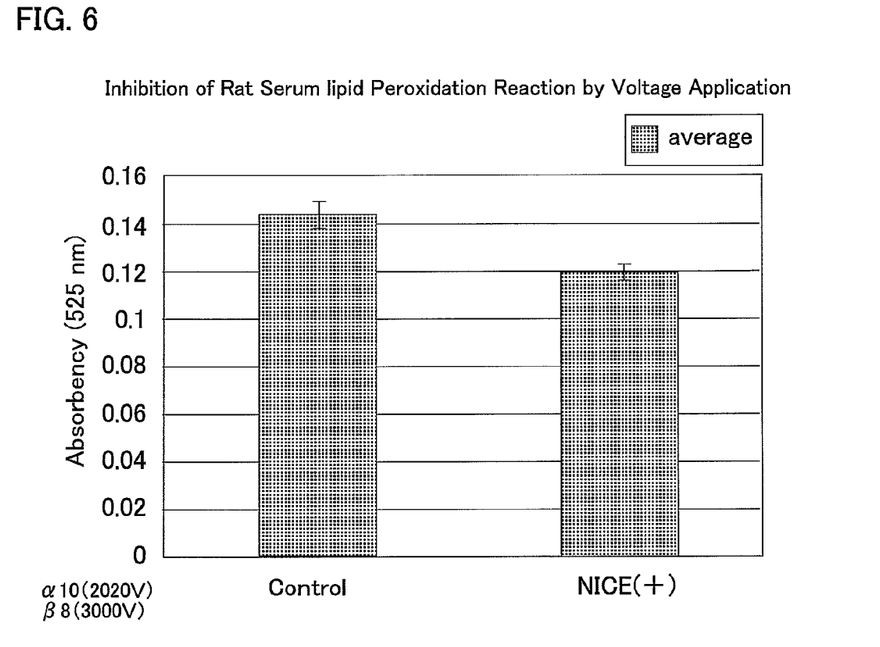
FIG. 6 shows data for Experiment 1 related to inhibition of rat serum lipid peroxidation by room temperature preservation.
Figure 7:
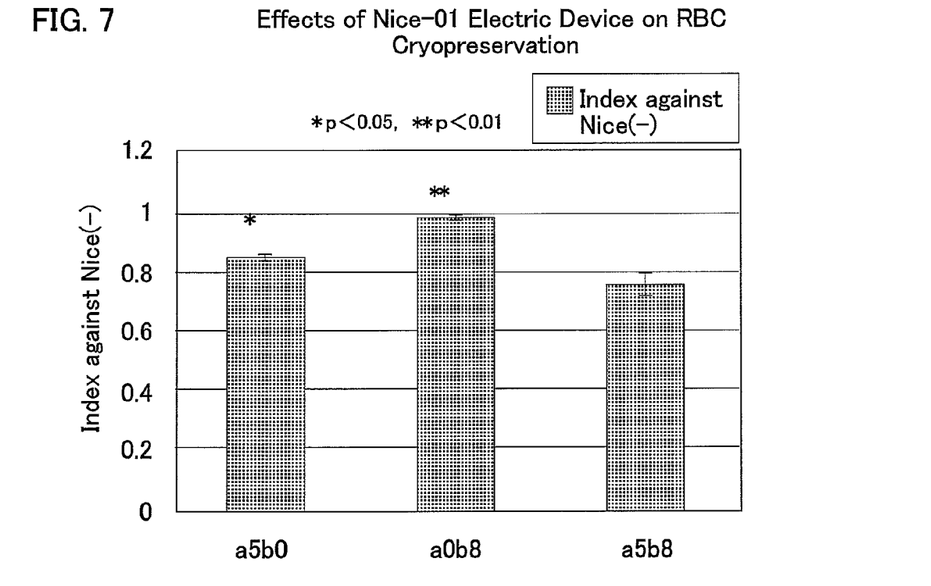
FIG. 7 shows data for Experiment 2 related to superiority in DC and AC simultaneous application in human red blood cell freezing.
Figure 8:
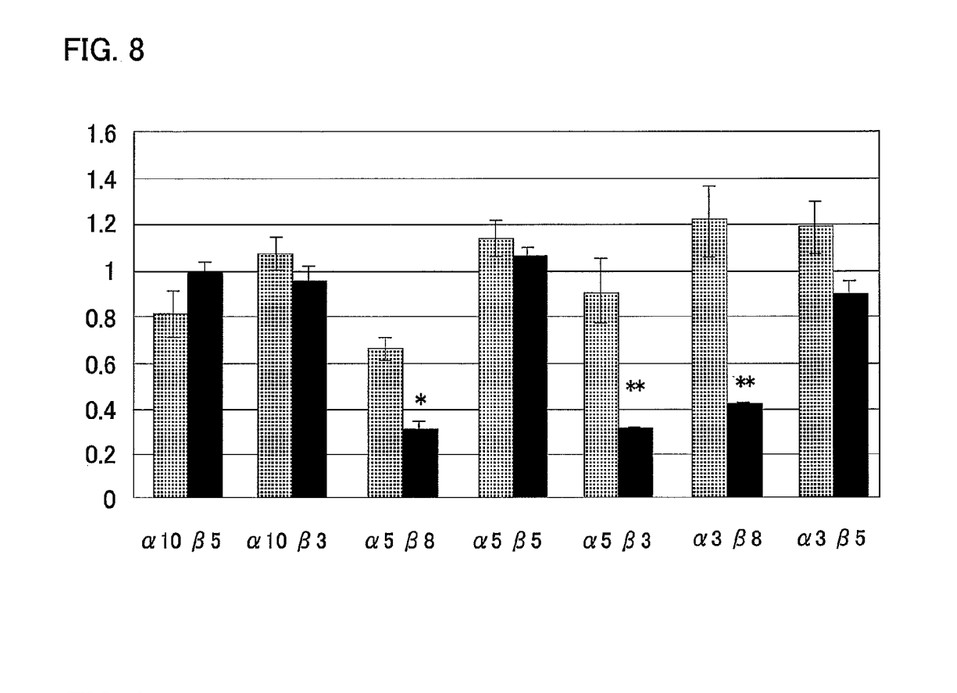
FIG. 8 shows data for Experiment 3 related to optimum conditions for applying voltage in human red blood cell freezing.
Figure 9:
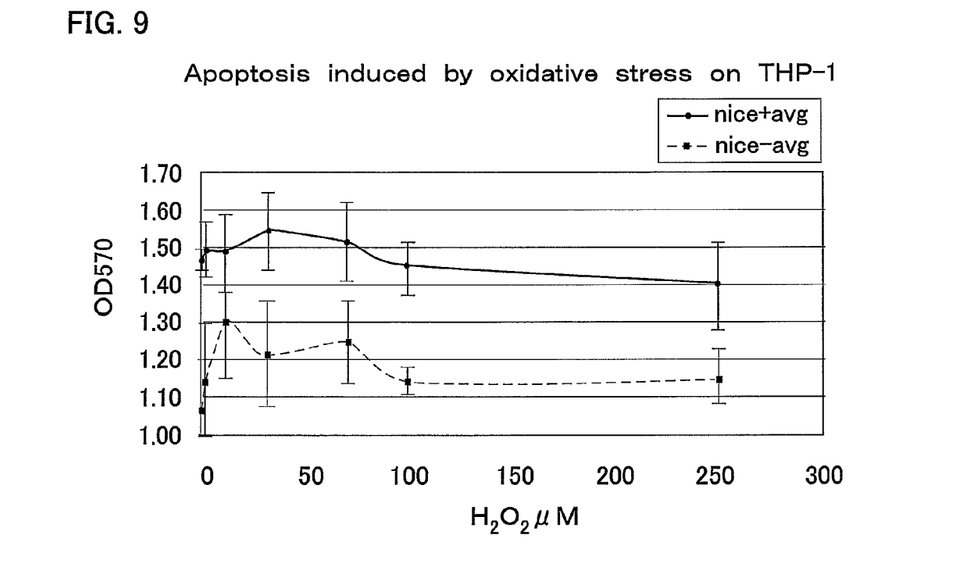
FIG. 9 shows data for Experiment 4 related to comparison in cell death under oxidation stress caused by cell culture.

FIG. 1 is a perspective view showing an example of the state of an application plate 2, a container 1, and an electrode during preservation process in a method of preserving a biomaterial O according to Example 1. FIG. 2 is a front sectional view showing the entire structure including a storage 4 in addition to the example according to Example 1 in FIG. 1 during preservation process. FIG. 3 is a perspective view showing an example of the state of an application plate 2, a container 1, and an electrode during preservation process in a method of preserving a biomaterial O according to Example 2. FIG. 4 is a front sectional view showing the entire structure including a storage 4 in addition to the example according to Example 2 shown in FIG. 3 during preservation process. FIG. 5 is a concept view showing the entire structure (including a storage 4) during preservation process in a method of preserving a biomaterial O according to Example 3. FIGS. 6 to 9 show data obtained from Experiments 1 to 4, respectively. More specifically, FIG. 6 shows data for Experiment 1 related to inhibition of rat serum lipid peroxidation caused by room temperature preservation. FIG. 7 shows data for Experiment 2 related to superiority in DC and AC simultaneous application in human red blood cell freezing, FIG. 8 shows data for Experiment 3 related to optimum conditions for applying voltage in human red blood cell freezing, and FIG. 9 shows data for Experiment 4 related to comparison in cell death under oxidation stress caused by cell culture.

Regarding Range Covered by Terms "preservation of blood, cells, tissues, and organs"

Regarding the range covered by the expression "preservation of a biomaterial O," the "biomaterial O" according to the present invention includes any of blood, cells, tissues and organs. Regarding the expression "preservation of a biomaterial O," the term "preservation" according to the present invention includes the following three meanings:

(1) Room temperature preservation (at 4° C. to 20° C. (at room temperature))

(2) preservation by freezing (at −20° C. to −196° C. (at liquid nitrogen temperature), and (3) cell culture preservation (at 37° C.).

In Experiment 1 (FIG. 6) that will be described, rat serum was preserved at room temperature as in the above (1). In Experiment 2 (FIG. 7) and Experiment 3 (FIG. 8), human red blood cells were preserved by freezing. Note that Experiments 2 and 3 were the same experiments but in Experiment 2, the use of $\alpha$(AC) alone was compared to the use of $\beta$(DC) alone and both $\alpha$ and $\beta$, while in Experiment 3, optimum conditions for simultaneous application were examined. In Experiment 4 (FIG. 9), culture preservation as in (3) was carried out.

EXAMPLE 1

A method of preserving a biomaterial O according to Example 1 of the present invention includes the step of simultaneously applying negative DC voltage and AC voltage in other words applying them in a superposed manner to the biomaterial O using a preservation device shown in FIGS. 1 and 2. In the simultaneous voltage application step, the biomaterial O is stored in a tube stand type retainer as a container 1, and a voltage application plate 2 supplied with negative DC voltage and AC voltage in a superposed manner is directly contacted to and laid along one outer surface of the container 1, so that the voltage is indirectly applied to the biomaterial O. Note that the application plate 2 may be indirectly laid along the container 1 for preservation without having the container 1 and the application plate 2 contact each other.

It was found that when the simultaneous voltage application according to the present invention is carried out, the indirect voltage application as described above more efficiently provides a homogeneous voltage application effect than voltage application by directly connecting an electrode to the container 1 or by directly placing the biomaterial O on the application plate 2.

More specifically, the simultaneous voltage application step is enabled by placing the container 1 (that is a tube stand type retainer in Example 1) that stores the biomaterial O on the voltage application plate 2 supplied with negative DC voltage and the AC voltage in a superposed manner.

Container 1

The container 1 stores the biomaterial O to surround at least the periphery of the biomaterial O and includes a conductive metal, particularly a highly conductive metal as a main component. In Example 1, the container 1 is made of a metal including aluminum with a purity of at least 80% as a main component. More specifically, the container is a tube stand type retainer produced by providing a 60 mm-thick aluminum plate with eight storing holes 1h at prescribed intervals used to store the biomaterial O.

Storing Holes 1h

The storing holes 1h are arranged to surround the periphery of the stored biomaterial O as it is covered at least with the walls and bottom of the container 1 (preferably the lid as well) at least in four directions around the material and at the lower surface direction (preferably the upper surface direction as well). Note that the "bottom" here (or the lower surface direction for the biomaterial O) refers to a component plate along which the voltage-applied application plate 2 is laid.

When viewed from the side of the biomaterial O in the storing hole 1h, a conductive plate (bottom plate) covers the direction (lower surface direction) in which voltage application indirectly acts and at least all the side surface directions excluding the opposite direction to the above direction (upper surface direction) are covered with the conductive plate (continuous wall plates placed in the four directions).

The storing hole 1h in Example 1 is made of a hollow cylindrical column. When the biomaterial O is blood, the blood is stored in a test tube and stored in the storing hole 1h or directly stored in the hole. The storing hole 1h preferably has identical sections in any depth of the hole.

Wall Thickness and Bottom Thickness

In order to achieve the effects based on the simultaneous application, the material of the container 1 preferably has a thickness of at least 10 mm (at least 10 mm for the bottom thickness and at least about 15 mm for the wall thickness, preferably about 15 mm for both the bottom thickness and the wall thickness).

In Example 1, the minimum wall thickness 1a in the vertical direction when seen in a plan view (the minimum distance in the horizontal direction from the side end of the storing hole 1h to the front surface side (or back surface side) of the container 1) is 15 mm. The minimum wall thickness 1b in the horizontal direction when seen in a plan view (the minimum distance in the horizontal direction from a side end of the storing hole 1h to the right side surface (or left side surface) of the container 1) is 30 mm. Furthermore, the minimum bottom thickness 1c in the height-wise direction (the minimum distance in the vertical direction from the bottom of the storing hole 1h to the bottom surface of the container 1) is 15 mm.

In addition, the characteristic length 1d (the diameter of the section for a circular storing hole 1h and the longer side length of the section for a square storage 1h) of the section of the storing hole 1h is 14 mm. The minimum wall thickness 1e between the storing holes 1h (the minimum distance in the horizontal direction from a side end of a first storing hole 1h to a side end of an adjacent second storing hole 1h) is 15 mm.

Application Plate 2

The application plate 2 is made of a conductive material and includes a pair of symmetrically arranged electrodes of electric wires 3. The electric wires 3 serve as common wires 3 for DC and AC voltage and the electrodes are also arranged to share DC and AC voltage. In this way, a part of AC voltage is transformed in a superposed manner into DC voltage by simultaneous application, so that the actual effective value of the AC voltage (upon the biomaterial O) is lower than a value set for the AC voltage and the actual effective value of the DC voltage (upon the biomaterial O) is larger than a value set for the DC voltage.

As for voltage to be applied, it is preferable that neither the absolute value of DC voltage nor the absolute value of AC voltage exceeds 5000 V. More specifically, the value set for the AC voltage is preferably in the range from 500 V to 2500 V, and the value set for the DC voltage is preferably in the range from 200 V to 1000 V. In addition, the value set for the DC voltage (in absolute value) is preferably larger than the value set for the AC voltage.

As for the combination of AC and DC voltage values, when the value set for the DC voltage is about 1000 V or 3000 V in absolute value, the value set for the AC voltage is preferably about in the range from 500 V to 550 V.

Note that the set values described above and those according to the present invention refer to effective values of voltage actually applied on the biomaterial O when AC or DC voltage alone is applied.

Storage 4

As shown in FIG. 2, the application plate 2 is placed on the storage 4 with a storage shelf and used to preserve the biomaterial O in this state.

EXAMPLE 2

In Example 2, as the simultaneous voltage application step, the container 1 (the container 1 in Example 2 is a rectangular box shaped retainer) whose bottom thickness and wall thickness are both 15 mm having the biomaterial O inside is placed on the voltage application plate 2 provided with negative DC voltage and AC voltage in a superposed manner. Note that in Example 2, the container 1 has a rectangular shape in a plan view and the length 1$d$ of the longer side of the rectangle (inner size) is set to 207 mm and the length 1$f$ of the shorter side of the rectangle is set to 112.5 mm.

According to the preservation method by simultaneous voltage application using the container 1 in Example 2, the biomaterial O having a relatively large volume can be preserved in the same arrangement as that of Example 1 except for the size of the container 1.

EXAMPLE 3

In Example 3, unlike Example 1, a container bag having at least a prescribed bag material thickness is used instead of the container 1. However, the inner side of the container bag is coated or laminated with a conductive material and the effect brought about by simultaneous application is effectively obtained as the bag contacts the biomaterial O almost in all directions. The biomaterial O is provided with voltage in an ion induction direction with DC voltage indicated by the arrow A in FIG. 5 and in an ion induction direction with AC voltage indicated by the arrow B in a superposed manner.

The above-described examples are examples for carrying out the preservation method according to the present invention, the present invention is not necessarily limited to the above, and various modifications can be obtained without departing from the spirit and scope of the present invention.

Experiment 1

"Inhibition of Rat Serum Lipid Peroxidation Reaction by Voltage Application" (FIG. 6)

Rat serum was preserved at room temperature and measured for its lipid peroxide content in Experiment 1.

Method in Experiment 1

Serum was separated from rat peripheral blood and obtained as a sample. The sample was dispensed in a tube and allowed to stand at room temperature (20° C.) for 12 hours for preservation. At the time, the application plate 2 was provided with a (AC voltage) at 2020 V and β (negative DC voltage) at 3000 V and the sample was preserved on the application plate 2 while being provided with the AC voltage and the negative DC voltage. After the 12-hour preservation, the lipid peroxide content was measured using TBARS (Thiobarbituric Acid Reactive Substances) assay and the result was compared to a sample without voltage application. In the measurement by the TBARS assay, malondialdehyde (MDA) produced by decomposition of lipid peroxide in the sample reacts with thiobarbituric acid to produce a red reactant, and by taking advantage of the property, the absorbency (525 nm) is measured using a spectrophotometer. In the measurement, Ultraspec 3000 manufactured by Pharmacia Biotech, Inc. was used to measure the absorbency and the values were compared among the groups.

Result of Experiment 1

As for the lipid peroxide content, the sample provided with the DC and AC voltage had a significantly lower absorbency than the sample without application, which indicates that production of lipid peroxide was inhibited (see FIG. 6).

This shows that oxidation of the lipid in the serum was reduced by the voltage application.

Experiment 2

"Superiority in AC and DC Simultaneous Application in Human Red Blood Cell Freezing" (see FIG. 7 entitled "Effects of NICE-01 Electric Device on RBC Cryopreservation")(NICE-01 refers to the preservation device according to Example 1 of the present invention.)

Note that the "1" in the ordinate in FIG. 7 represents the case without voltage application.

Method in Experiment 2

An equal amount of freezing preservation liquid (albumin-containing CP-1 from KYOKUTO PHARMACEUTICAL INDUSTRIAL CO., LTD.) was added to human peripheral washed blood cells sampled from a volunteer and then the mixture was frozen in three hours at −20° C. At the time, an aluminum application plate was provided in a freezer, and three kinds of electric fields were produced by applying AC voltage (α5: 980 V) alone, by applying DC voltage (β8: −3000 V) alone, and by applying both AC and DC simultaneously (superposed) (α5 and β8). Then, freezing was carried out on the application plate.

The frozen sample was then stored in the freezer at −80° C. for two weeks, defrosted in a 37° C. constant temperature bath, then subjected to centrifugal separation and measured for its LDH (lactic dehydrogenase) content in the supernate liquid. The LDH measurement was carried out using an LDH release assay kit manufactured by Promega Corporation, and the absorbency was measured using a TERMO MAX microplate reader manufactured by Molecular Devices. The measured results were compared among the case of application of AC voltage (α5: 980 V) alone, the case of application of DC voltage (β8: −3000 V) alone, and the case of the simultaneous AC and DC (superposed) application (α5 and β8).

Result of Experiment 2

The amount of LDH departed from peripheral red blood cells after freezing and defrosting was reduced in any of the groups of application of AC alone, DC alone and simultaneous AC and DC application as compared to the case of voltage application (−)(that corresponds to no voltage application), which indicates reduced cell damage. In the case of the AC and DC simultaneous application, a significant reduction in cell damage was observed as compared to the case of application of AC alone or DC alone.

As can be confirmed from the above result, the cell damage in freezing with voltage application was more significantly reduced when both α and β were applied simultaneously.

Experiment 3

"Optimum Conditions for Applying Voltage in Human Red Blood Cell Freezing" (FIG. 8)

Method in Experiment 3

Similarly to Experiment 2, an equal amount of freezing preservation liquid (albumin-containing CP-1 from KYOKUTO PHARMACEUTICAL INDUSTRIAL CO., LTD.) was added to human peripheral washed blood cells sampled from a volunteer and then the mixture was frozen in three hours at −20° C. At the time, an aluminum application plate was provided in a freezer and electric fields were produced by applying both AC voltage (α) shown in Table 1 and DC voltage (β) shown in Table 2 using the voltage application preservation device according to Example 1 of the present invention. Then, freezing was carried out on the application plate. The voltage application was carried out based on the combinations of α and β shown in FIG. 8. Note that if the absolute value of the DC voltage is greater than the absolute value of the AC voltage, the AC voltage superposed with the negative DC voltage has its amplitude fluctuated in the negative region. Therefore, if DC voltage of β5 and β8 is superimposed and applied, the voltage has its amplitude fluctuated in the negative region.

TABLE 1

| | α (AC voltage) set scale | | |
|---|---|---|---|
| | 3 | 5 | 10 |
| set voltage when applied alone | 530 V | 980 V | 2020 V |

TABLE 2

| | β (DC voltage) set scale | | |
|---|---|---|---|
| | 3 | 5 | 8 |
| set voltage when applied alone | −950 V | −1500 V | −3000 V |

The frozen sample was then preserved for two weeks in the freezer at −80° C., then defrosted in a 37° C. constant temperature bath, followed by centrifugal separation and measured for its LDH (lactic dehydrogenase) in its supernate liquid. The LDH measurement was carried out using an LDH release assay kit manufactured by Promega Corporation, and the absorbency was measured using a TERMO MAX microplate reader manufactured by Molecular Devices. At the time, the absorbency itself varies depending on the temperature condition or the like during measurement for each experiment, and therefore a control, in other words, the case without voltage application (the left one of each two parallel bars in the graph in FIG. 8) and the case with voltage application (the right one of each two parallel bars in the graph in FIG. 8) were carried out at the same time for each experiment, and the effect of the voltage application was examined by comparing them.

Result of Experiment 3

The result of experiment 3 is given in FIG. 8. In FIG. 8, as for the LDH content in each combination of α (AC voltage) and β (negative DC voltage), two bars are shown for the case without voltage application (the light-color bar on the left) and the case with voltage application (the dark-color bar on the right). In FIG. 8, the Y-axis (ordinate) represents actually measured values of absorbency. As the value is greater, the amount of enzymes (LDH) separated from broken red blood cells is greater, which indicates greater cell damage. The absorbency itself could vary depending on the temperature condition or the like during measurement for each experiment, and therefore a control, in other words, the case without voltage application (the left one of each two parallel bars in the graph in FIG. 8) and the case with voltage application (the right one of each two parallel bars in the graph in FIG. 8) were carried out at the same time for each experiment, and the effect of the voltage application was examined by comparing them. As can be seen from each two parallel bars in FIG. 8, as the difference between NICE (−)(without voltage application) and NICE (+)(with voltage application) is greater, the effect of application is greater.

LDH separated from peripheral red blood cells after defrosting decreases as compared to the groups without voltage application except for the combination of α (AC) and β (DC) being α10 and β5, which indicated that red blood cell damage during freezing was reduced by voltage application. In the combinations of α5 (980 V) and β8 (3000 V), α5 (980 V) and β3 (950 V), and α3 (530 V) and β8 (3000 V), more significant reduction in free LDH was observed.

Experiment 4

"Inhibition of Cell Damage under Oxidation Stress by Voltage Application" (FIG. 9)

In Experiment 4, cell damage was induced by adding hydrogen peroxide to cells in culture and comparison experiments as to cell death were carried out.

Object of Experiments

In order to examine how simultaneous voltage application at NICE-01 affects living cells and reduction in oxidation stress, the effect of voltage application was considered when cells in culture were provided with oxidation stress by hydrogen peroxide.

Method of Experiment

THP-1 cells as a human macrophage cell strain were cultured using a 96-well plate for 12 hours at 37° C. in an RPM11640 culture liquid with the presence of 5% $CO_2$ while 0 uM to 250 uM hydrogen peroxide was added, and cell damage by oxidation stress was induced. An incubator manufactured by Napco was used, an aluminum application plate was placed in the incubator, and the 96-well plate was placed on the application plate. Then, cells were cultured while AC voltage and negative DC voltage (α5 and β8) were simultaneously applied. The cell damage was evaluated by MTT method. An MTT agent (5 mg/ml) was added in the amount of 20 ul/well to each well in the plate after twelve hours from starting of the culture and then the cells were cultured for four more hours. After the end of culture, an SDS agent was added to each well and the cells were dissolved. Then, formazan produced by reduction with dehydrogenase in mitochondria was measured for absorbency using an absorbency plate reader (TERMO MAX microplate reader manufactured by Molecular Devices) at a wavelength of 490 nm.

Result of Experiment 4 (FIG. 9)

As for the effect of addition of hydrogen peroxide on the cell viability, the cell viability is raised in low concentrations up to 100 uM, and conversely cell death is induced in high concentrations. In the present experiment, the absorbency according to MTT method was slightly raised in low concentrations and lowered in high concentrations. The voltage applied groups had higher absorbency values in any of concentrations of hydrogen peroxide as compared to the case without voltage application (application (−)), and the cell viability was raised or maintained.

In the experiments, the cell viability was measured by the MTT method, according to which higher absorbency values correspond to higher viability and conversely lower absorbency values correspond to lower viability. Here, cells generally take advantage of low concentration oxidizing stress as a stimulus for cell proliferation or the like, but unhealthily high level oxidizing stress induces cell damage or cell death. Therefore, in low concentrations up to 100 uM, the cell viability is raised, while in a concentration as high as 250 uM, cells are damaged and the absorbency is lowered. As can be seen from the result, voltage application allows cells to be less likely to die despite high concentration oxidizing stress applied.

This phenomenon may be caused by neutralization or inhibition of oxidizing reaction by voltage application as in Experiment 1 (FIG. 6), while there may be a new mechanism that transforms electric energy into biological energy in addition to the above. More specifically, it is important to increase energy (ATP) in cells to prevent the cells from dying, and the likelihood of cell death may be reduced because of voltage application.

Example of Specific Procedure for Preserving Blood by Freezing

An example of a specific procedure for preserving blood by freezing will be described. About 400 ml of peripheral blood is sampled from a blood donor by cubital vein puncture and stored in a blood storing bag. The sample is separated into the plasma component and the blood cell component by a centrifugal device and removed of the plasma component, physiologic saline and cryoprotectant (CP-1 manufactured by KYOKUTO PHARMACEUTICAL INDUSTRIAL CO., LTD.) are added to the remaining component and the mixture was frozen. At the time, the freezing is carried out while simultaneously applying a (AC) voltage and β (DC) voltage.

Figure 10:
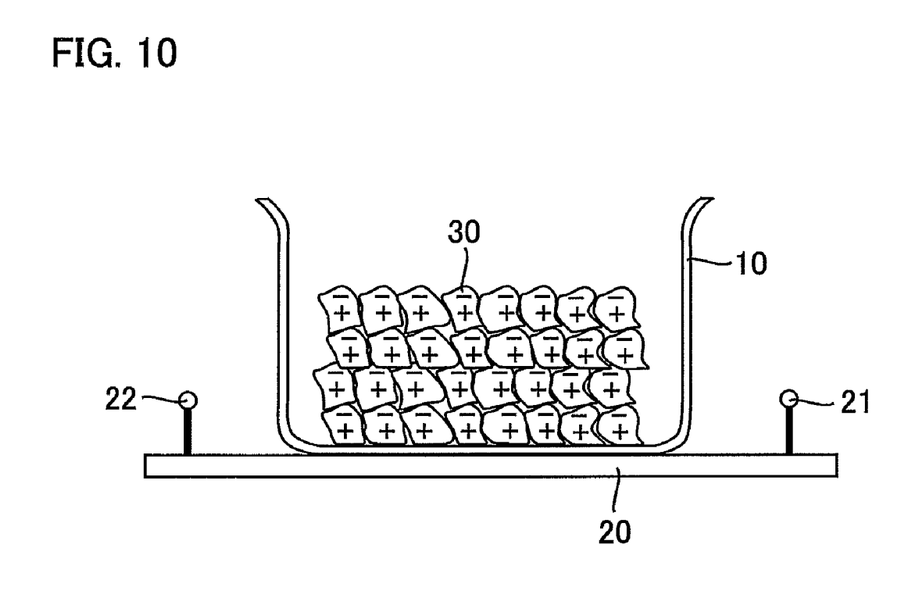
FIG. 10 is a view for illustrating the effect of negative DC voltage application.

As described above, the biomaterial is frozen while being supplied with negative DC voltage and AC voltage at the same time, so that cell damage can be reduced. This is for the following reason. FIG. 10 is a view for illustrating the effect of the negative DC voltage application.

A container 10 that stores multiple cells 30 is placed on an application plate 20. The application plate 20 has terminals 21 and 22, the terminal 21 is used to apply negative DC voltage and the terminal 22 is used to apply AC voltage.

A cell has an entrance used to exchange water and ions that is closed when the pH outside the cell is raised and opened when the pH is lowered. When AC voltage is applied to cells, positive charges and negative charges appear at the cells by the AC voltage, and the cells can be prevented from being oxidized by the electrons.

However, after the state of the cells with charges continues for a prescribed period or more, the electrons start to come out from the cells and the number of the positive charges becomes relatively larger in the cells. It is believed that the entrances of the cells are opened as a result and allow the body fluid outside the cells to come into the cells, and the cells are swollen.

As shown in FIG. 10, when negative DC voltage is applied as it is superposed on the AC voltage, among the positive charges and the negative charges that appear in the cells 30 by the AC voltage, the positive charges are localized on the side of the application plate 20, and the negative charges are localized on the opposite side to the application plate 20. As a result, the positive charges and the negative charges are balanced and remain in the cells 30.

In this way, the electrons within the cells 30 do not come out from the cells even a prescribed period after the positive charges and the negative charges appear in the cells 30, and the entrances of the cells 30 are also kept closed.

Therefore, when the negative DC voltage is superposed on the AC voltage and applied, the body fluid does not enter the cells 30, so that the volume of the cells 30 can be prevented from increasing and the survival rate of the cells 30 increases.

In addition, when AC voltage with a frequency lower than 10 GHz is applied to water molecules, the water molecules vibrate according to the applied AC voltage. Consequently, when water is frozen while AC voltage is applied, clusters of water molecules are unlikely to form, so that the water can be prevented from having an increased volume by freezing. Therefore, by the same mechanism, biological fluid present within the cells 30 can be prevented from having an increased volume by freezing.

As in the foregoing, simultaneous application of negative DC voltage and AC voltage allows positive and negative charges to be held in balance in the cells 30 and the entrances to be kept closed, while the biological fluid in the cells 30 can be prevented from having an increased volume by freezing, so that cell damage by freezing can be reduced.

It is to be understood that the embodiments disclosed herein are illustrative and not restrictive. The scope of the invention is defined by the appended claims rather than by the description preceding them, and all modifications that fall within the scope of claims and equivalence thereof are intended to be embraced by the claims.

Industrial Applicability

The simultaneous application technique according to the present invention can be applied in the medical industry as follows. As for freezing with voltage application, the invention may be applied to freezing of homologous peripheral blood for transfusion, auto-blood, bone marrow cell fluid for marrow transplant, cord blood, islet cells, cultured cells, ES cells, organs for transplant, and various grafts such as bones, aortas, tracheas, cardiac valves, cornea, and skin.

As for cryo-preservation with voltage application, the invention may be applied to cooling preservation of homologous peripheral blood for transfusion, auto-blood, organs for transplant and the like.

The invention claimed is:

1. A method of preserving a biomaterial comprising the step of simultaneously applying negative DC voltage and AC voltage to a biomaterial (O) and, wherein said simultaneous voltage application step is carried out by placing a container (1) that stores said biomaterial (O) on a voltage application plate (2) supplied with said DC voltage and said AC voltage in a superposed manner from electrodes of electric wires (3) serving as common wires for said DC voltage and said AC voltage, said electrodes being symmetrically arranged relative to said voltage application plate (2), and said container (1) being made of a conductive metal and having a bottom thickness of at least 10 mm and a wall thickness of at least 15 mm.

2. The method of preserving a biomaterial according to claim 1, wherein a part of said AC voltage is transformed in a superposed manner into DC voltage by simultaneous application, such that an actual effective value of said AC voltage upon said biomaterial (O) is lower than a value set for said AC voltage and an actual effective value of said DC voltage upon said biomaterial (O) is larger than a value set for said DC voltage.

3. A method of preserving a biomaterial comprising the step of simultaneously applying negative DC voltage and AC voltage to a biomaterial (O) and, wherein in said simultaneous voltage application step, said biomaterial (O) is stored in a container (1) that surrounds at least a periphery of said biomaterial (O), and a voltage application plate (2) supplied with said DC voltage and said AC voltage in a superposed manner from electrodes of electric wires (3) serving as common wires for said DC voltage and said AC voltage is laid directly or indirectly along one outer surface of said container (1), so that the voltage is indirectly applied to the biomaterial (O), said electrodes being symmetrically arranged relative to said voltage application plate (2), and said container (1) being made of a conductive metal and having a bottom thickness of at least 10 mm and a wall thickness of at least 15 mm.

4. The method of preserving a biomaterial according to claim 3, wherein said simultaneous voltage application step is carried out by placing the container (1) that stores said biomaterial (O) on the voltage application plate (2) supplied with said DC voltage and said AC voltage in a superposed manner.

5. The method of preserving a biomaterial according to claim 3, wherein a part of said AC voltage is transformed in a superposed manner into DC voltage by simultaneous application, such that an actual effective value of said AC voltage upon said biomaterial (O) is lower than a value set for said AC voltage and an actual effective value of said DC voltage upon said biomaterial (O) is larger than a value set for said DC voltage.

* * * * *